United States Patent [19]

Cignarella

[11] Patent Number: 5,672,601
[45] Date of Patent: Sep. 30, 1997

[54] 3-8-DIAZABICYCLO [3.2.1] OCTANE DERIVATIVES HAVING ANALGESIC ACTIVITY

[75] Inventor: Giorgio Cignarella, Milan, Italy

[73] Assignee: Riace Establishment, Vaduz, Liechtenstein

[21] Appl. No.: 696,948

[22] PCT Filed: Feb. 10, 1995

[86] PCT No.: PCT/EP95/00476

§ 371 Date: Aug. 22, 1996

§ 102(e) Date: Aug. 22, 1996

[87] PCT Pub. No.: WO95/23152

PCT Pub. Date: Aug. 31, 1995

[30] Foreign Application Priority Data

Feb. 23, 1994 [IT] Italy ................... MI94A0326

[51] Int. Cl.$^6$ ............... A61K 31/495; C07D 487/08
[52] U.S. Cl. .............................. 514/249; 544/349
[58] Field of Search .......................... 544/349; 514/249

[56] References Cited

PUBLICATIONS

"Diazabicyclooctanes", *Chemical Abstracts*, vol. 58, No. 11, Abstract No. 11382a, col. 2, May 27, 1963.

G. Cignarella et al., "Bicyclic Homologs of Piperazine. VI.[1] Synthesis and Analgesic Activity of 3–Substituted 8–Propionyl–3,8–diazabicyclo[3.2.1]octanes", *Journal of Medicinal Chemistry*, vol. 6, No. 6, Nov. 1963, pp. 764–766.

G. Cignarella et al., "Thermal and Chemical Intramolecular N→N Acyl–Migration in 8–Acyl–3, 8–Diazabicyclo[3.2.1] octanes", *Tetrahedron*, vol. 19, No. 1, Jan. 1963, pp. 143–148.

G. Cignarella et al., "Bicyclic Homologs of Piperazine. VIII.[1] Synthesis and Analgesic Activity of 3–Aralkenyl–8–proprionyl–3,8–diazabicyclo[3.2.1]octanes", *Journal of Medicinal Chemistry*, vol. 8, No. 3, May 1965, pp. 326–331.

E. Occelli et al., "Omologhi Biciclici Della Piperazina", *IL FARMACO, ED. SCI.*, vol. 33, No. 6, Jun. 1978, pp. 401–420.

G. Cignarella et al., "Interaction of 3,8–Diazabicyclo (3.2.1) Octanes with MU and Delta Opioid Receptors", *Pharmacological Research Communications*, vol. 20, No. 5, May 1988, pp. 383–394.

L. Toma et al., "Molecular Mechanics and $^1$H NMR Conformational Study of 3,8–Diazabicyclo[3,2,1]octanes and Related cis–2,6–Dimethylpiperazines Active on Opioid Receptors", *Tetrahedron*, vol. 48, No. 1, Jan. 1992, pp. 159–166.

D. Barlocco et al., "Computer–aided structure–affinity relationships in a set of piperazine and 3,8–diazabicyclo[3.2.1] octane derivatives binding to the μ–opioid receptor", *Journal of Computer–Aided Molecular Design*, vol. 7, No. 5, Oct. 1993, pp. 557–571.

*Primary Examiner*—Robert T. Bond
*Attorney, Agent, or Firm*—Young & Thompson

[57] ABSTRACT

Compounds of general formula (I)

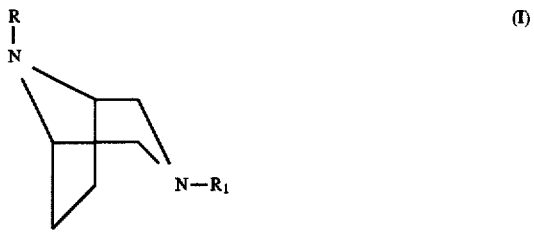

wherein R and $R_1$, different from each other, are a straight or branched $C_2$–$C_8$ acyl group; a group of formula —$CH_2$—(A)—B wherein: A is a single bond between two carbon atoms, or a group of formula —CH—CH, —$CH_2$—CO—, B is a $C_6$–$C_{10}$ aryl group, optionally substituted, at the ortho-meta- and para-positions, with one or more substituents, which are the same or different, selected from the group consisting of CONHR, carboxyl, cyano, nitro, NHCOR; an aromatic heterocyclic or alicyclic group with 5 or 6 members in the ring, optionally benzocondensed, having at least one heteroatom selected from nitrogen, oxygen, sulfur, said heterocyclic group optionally having one or more substituents as described above for the aryl group; with the proviso that when one of R or $R_1$ is the propionyl group, the other can not be the cinnamyl group or the p-nitrocinnamyl group, and when R is the propionyl group, $R_1$ cannot be o-, or m-nitrocinnamyl; and the pharmaceutically acceptable salts thereof. Compounds of formula (I) have central analgesic activity.

12 Claims, No Drawings

3-8-DIAZABICYCLO [3.2.1] OCTANE DERIVATIVES HAVING ANALGESIC ACTIVITY

This application is a 371 of PCT/EP95/00476 filed 10 Feb. 1905 which claims the priority of Italian Application ml 94 A 000326 filed 23 Feb. 1994.

The present invention relates to 3,8-diazabicyclo[3.2.1] octane derivatives, the use thereof as agents with central analgesic activity in the manufacturing of medicaments and pharmaceutical compositions containing them.

More particularly, the present invention relates to compounds of general formula (I)

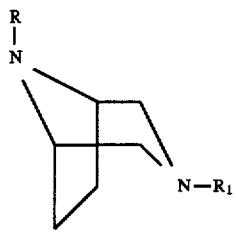

wherein

R and $R_1$, different from each other, are a straight or branched $C_2$-$C_8$ acyl group;
a group of formula

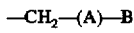

—$CH_2$—(A)—B wherein:

A is a single bond between two carbon atoms, or a group of formula —CH=CH—, —$CH_2$—CO—, B is a $C_6$-$C_{10}$ aryl group, optionally substituted, at the ortho-, meta- and para-positions, with one or more substituents, which are the same or different, selected from the group consisting of CONHR, carboxyl, cyano, nitro, NHCOR; an heterocyclic aromatic or alicyclic group with 5 or 6 members in the ring, optionally benzocondensed, having at least one heteroatom selected from nitrogen, oxygen, sulphur; said heterocyclic group optionally having one or more substituents as described above for the aryl group; with the proviso that when one of R or $R_1$ is the propionyl group, the other cannot be the cinnamyl group or the p-nitrocinnamyl group, and when R is the propionyl group, $R_1$ cannot be o-, or m-nitrocinnamyl; and the pharmaceutically acceptable salts thereof.

Examples of $C_1$-$C_8$ acyl groups are acetyl, propionyl, isopropionyl, butyryl, isobutyryl, valeryl, isovaleryl, pivaloyl, caproyl.

Examples of heterocyclic groups are pyrrole, furan, thiophene, imidazole, oxazole, thiazole, pyridine, pyrimidine, pyrazine.

Examples of pharmaceutically acceptable salts are those with halohydric acids, such as hydrochloric acid, hydrobromic acid; mineral acids, such as sulfuric and phosphoric acids; organic acids, such as acetic, propionic, succinic, glutaric, benzoic, salicylic acids. If the carboxylic group is present, examples of salts are those with bases of alkali or alkaline-earth metals, such as sodium, potassium, calcium, magnesium; bases of non-toxic metals; non-toxic organic amines.

Preferred compounds of formula (I) are those wherein R or $R_1$ are an acyl group as defined above and a group of formula —$CH_2$—(A)—B, wherein A is a —CH=CH— group and B is a phenyl group, optionally substituted, as defined above or a non-benzocondensed heterocyclic group.

Preferred compounds of formula (I) are also those wherein R or $R_1$ are an acyl group as defined above and a group of formula —$CH_2$—(A)—B, wherein A is a single carbon-carbon bond and B is an indenyl group or a benzocondensed heterocyclic group as defined above.

Particularly preferred are the following compounds:

$N^8$-pivaloyl-$N^3$-(p-nitro)cinnamyl-3,8-diazabicyclo[3.2.1] octane;

$N^8$-propionyl-$N^3$-3-(2-thienyl)allyl-3,8-diazabicyclo[3.2.1] octane;

$N^8$-propionyl-$N^3$-3-[(5-nitro)-2-thienyl]allyl-3,8-diazabicyclo[3.2.1]octane;

$N^8$-3-[(5-nitro)-2-thienyl]allyl-$N^3$-propionyl-3,8-diazabicyclo[3.2.1]octane;

$N^8$-propionyl-$N^3$-(2-indolyl)methyl-3,8-diazabicyclo[3.2.1] octane;

$N^8$-(2-indolyl)methyl-$N^3$-propionyl-3,8-diazabicyclo[3.2.1] octane;

$N^8$-propionyl-$N^3$-(2-benzofuranyl)methyl-3,8-diazabicyclo [3.2.1]octane;

$N^8$-(2-benzofuranyl)methyl-$N^3$-propionyl-3,8-diazabicyclo [3.2.1]octane;

$N^8$-acetyl-$N^3$-cinnamyl-3,8-diazabicyclo[3.2.1]octane;

$N^8$-valeryl-$N^3$-cinnamyl-3,8-diazabicyclo[3.2.1]octane;

$N^8$-butyryl-$N^3$-cinnamyl-3,8-diazabicyclo[3.2.1]octane;

$N^8$-butyryl-$N^3$-(p-nitro)cinnamyl-3,8-diazabicyclo[3.2.1] octane;

$N^8$-(p-nitro)cinnamyl-$N^3$-butyryl-3,8-diazabicyclo[3.2.1] octane;

$N^8$-(m-nitro)cinnamyl-$N^3$-propionyl-3,8-diazabicyclo [3.2.1]octane;

$N^8$-(o-nitro)cinnamyl-$N^3$-propionyl-3,8-diazabicyclo [3.2.1.]octane.

$N^8$-valeryl-$N^3$-(p-nitro)cinnamyl-3,8-diazabicyclo[3.2.1] octane;

$N^8$-propionyl-$N^3$-(p-carboxy)cinnamyl-3,8-diazabicyclo [3.2.1]octane;

$N^8$-propionyl-$N^3$-(p-cyano)cinnamyl-3,8-diazabicyclo [3.2.1]octane;

The compounds specifically excluded from formula (I) reported above, were described as analgesic agents in J. Med. Chem., 1965, 8, 326. Said compounds were exhaustively studied due to their affinity to opioid μ and δ receptors and their strong analgesic activity has been described (G. Cignarella et al., Pharmacol. Res. Comm., 1985, 5, 383).

Now it has been found that the compounds of formula (I) described above have central analgesic activity as strong as that of morphine and, surprisingly, they are substantially free from withdrawal phenomena and less liable to induce tolerance or addiction following chronic treatment.

"Substantially free from" means an activity 3 to 20 times lower than that of morphine in the jumping test in the mouse, after chronic administrations three times a day for 7 consecutive days of analgesically equipotent doses.

The present invention also relates to the compounds of general formula (I) as agents with central analgesic activity.

Another object of the present invention are the processes for the preparation of said compounds.

A further object of the present invention is the use of the compounds of formula (I) for the preparation of a medicament useful to induce analgesia at the level of the central nervous system in a mammal, particularly in man, which requires said treatment.

Still another object of the present invention are pharmaceutical compositions containing a therapeutically effective amount of at least one compound of formula (I) in mixture with conventional carriers and excipients.

The compounds of general formula (I) can be prepared by methods known to those skilled in the art.

For example, the processes described in the above cited J. Med. Chem. and Pharmacol. Res. Comm. can be used.

In a general scheme, starting from 3,8-diazabicyclo[3.2.1.]octane suitably acylated with a straight or branched $C_2$–$C_8$ acyl residue at one of the two nitrogen atoms at the 3 or 8 position, this is reacted with a compound of formula (II)

X—$CH_2$—(A)—B  (II)

wherein A and B are as defined above and X is a halogen atom, preferably chlorine or bromine, to obtain a compound of formula (I).

Alternatively, 3,8-diazabicyclo[3.2.1.]octane, having the —$CH_2$—(A)—B group on one of the nitrogen atoms, is reacted with the suitable straight or branched $C_2$–$C_8$ acyl chloride.

$N^8$-acyl-3,8-diazabicyclo[3.2.1.]octanes were described in G. Cignarella et al., J. Med. Chem., 1965, 8, 326.

$N^3$-acyl-3,8-diazabicyclo[3.2.1.]octanes are described in G. Cignarella et al., Tetrahedron, 1963, 19, 143.

Compounds of formula (II) are generally known in literature or commercially available.

Particularly, compounds of general formula (I), wherein $R_1$ is a —$CH_2$—(A)—B group, wherein A is a carbon-carbon bond, B is a benzocondensed heterocyclic group, optionally substituted, are prepared treating 3,8-diazabicyclo[3.2.1.-]octane, having the $N^8$ nitrogen atom protected with a suitable protecting group, for example t-butoxycarbonyl, or other analogue groups known to those skilled in the art, with a compound of formula (III)

X—CO—(A)—B  (III)

wherein the groups are as defined above; deprotecting the $N^8$ nitrogen, subsequently reducing the $N^3$ amido group to amine, and finally acylating the free $N^8$ nitrogen.

Alternatively, compounds of formula (I), wherein R is a —$CH_2$—(A)—B group, wherein A is a carbon-carbon bond, B is a benzocondensed heterocyclic group, optionally substituted, are prepared treating 3,8-diazabicyclo[3.2.1.]octane having the $N^3$ nitrogen atom protected by a benzyl group, or analogue, with a compound of formula (III) cited above, subsequently debenzylating the $N^3$ nitrogen atom; reducing the $N^8$ amide group to an amino group and acylating the $N^3$ nitrogen atom.

The reactions described above are carried out according to conventional techniques known to those skilled in the art. Generally, the reagents are in stoichiometric ratios, or slightly different ratios, depending in the receptivity of the specific reagent.

The acylation of the nitrogen at 3 or 8 is usually carried out with acyl chlorides in an inert reaction medium, such as an open- or close-chain ether, a ketone, an optionally halogenated hydrocarbon. The presence of a proton binding agent is preferred, such as a tertiary amine. Alternatively, the acylating agent can be a carboxylic acid anhydride.

The N-alkylation is carried out, similarly to the above N-acylation, in an inert reaction medium.

The N-deprotection is performed conventionally, for example in hydrochloric ether, when BOC is the protecting group, or by hydrogenation on Pd/c, in the case of a benzyl group.

The reduction of the amide group to amine is carried out with a hydride of an organ-aluminium compound in an inert anhydrous organic solvent.

The compounds of the present invention were tested for the capability thereof to bind to the opioid μ opioid receptor.

The test was carried out according to the method by Wood et al., Neuropharmacology, 1981, 20, 1219, with slight changes.

The compounds of the invention prove to bind selectively to the μ receptor with an affinity similar to that of morphine.

What stated above clearly shows that the compounds I, free or salified with pharmaceutically acceptable acids, can advantageously be used as active principles in medicaments having a central analgesic activity as well as a poor liability to induce tolerance and withdrawal phenomena, which are the most serious restrictions to the use of morphine. The lack of induction or tolerance and withdrawal could not at all be predicted from the up to now available literature on the affinity to μ and δ opioid receptors.

For the intended therapeutical uses, the compounds (I) or the salts thereof will be formulated in a therapeutically effective amount, in suitable pharmaceutical formulations, making use of conventional techniques and excipients, such as those described in "Remington's Pharmaceutical Sciences Handbook" XVII and Mack Pub., New York, U.S.A.

Examples of pharmaceutical compositions are tablets, capsules, granulates, soluble powders, drops, elixir, syrups, injectable forms, suppositories.

The dosages and the posology will be established by the physician, depending on the severity of the disease, the patient's conditions and possible interactions with other medicaments.

The following examples further illustrate the invention.

EXAMPLE 1

$N^8$-acetyl-3,8-diazabicyclo[3.2.1]octane was reacted with equimolar amounts of cinnamyl chloride, in the presence of potassium carbonate in acetone under reflux, checking the reaction by thin layer chromatography (TLC). When the reaction was completed, the inorganic salt was filtered off and the filtrate evaporated to dryness. The residue was purified by chromatography (1:1 $CHCl_3$/Ethyl acetate). $N^8$-Acetyl-$N^3$-cinnamyl-3,8-diazabicyclo[3.2.1]octane was obtained, the elementary analysis being in accordance with the desired compound.

The corresponding oxalate was prepared with conventional techniques.

Elementary analysis:

|  | C | H | N |
|---|---|---|---|
| Calculated | 63.31 | 6.78 | 7.7 |
| Found | 61.69 | 6.54 | 7.35 |

EXAMPLE 2

Analogously to what described in example 1, $N^8$-valeryl-$N^3$-cinnamyl-3,8-diazabicyclo[3.2.1]octane hydrochloride was prepared, m.p. 206°–209° C.

Elementary analysis

|  | C | H | N |
|---|---|---|---|
| Calculated | 63.31 | 6.78 | 7.7 |
| Found | 61.69 | 6.54 | 7.35 |

Analogously, the following compounds were prepared:
$N^8$-butyryl-$N^3$-cinnamyl-3,8-diazsbicyclo[3.2.1]octane hydrochloride, m.p. 202° C. (dec);
$N^8$-butyryl-$N^3$-(p-nitro)cinnamyl-3,8-diazabicyclo[3.2.1]octane, m.p. 82°–83° C.;

N⁸-(p-nitro)cinnamyl-N³-butyryl-3,8-diazabicyclo[3.2.1] octane, m.p. 94°–96° C.;

N⁸-(m-nitro)cinnamyl-N³-propionyl-3,8-diazsbicyclo [3.2.1]octane, hydrochloride m.p. 212°–214° C.;

N⁸-valeryl-N³-(p-nitro)cinnamyl-3,8-diazabicyclo[3.2.1] octane, m.p. 76°–78° C.;

N⁸-pivaloyl-N³-(p-nitro)cinnamyl-3,8-diazabicyclo[3.2.1] octane, m.p. 128°–129° C.;

N⁸-propionyl-N³-3-(2-thienyl)allyl-3,8-diazabicyclo[3.2.1] octane, m.p. 74°–75° C.;

N⁸-propionyl-N³-3-(5-nitro-2-thienyl)allyl-3,8-diazabicyclo[3.2.1]octane, m.p. 78°–80° C.;

N⁸-3-(5-nitro-2-thienyl)allyl-N³-propionyl-3,8-diazabicyclo[3.2.1]octane, m.p. 95°–97° C.

EXAMPLE 3

N⁸-BOC-3,8-diazabicyclo[3.2.1]octane was treated with equimolar amounts of benzofuran-2-carboxylic acid chloride in ether in the presence of triethylamine.

The recovered was product treated with hydrochloric ether and the resulting N³-(2-benzofuranocarbonyl)-3,8, diazabicyclo[3.2.1]octane was subjected, after removing the solvent, to reduction with SMEAH in toluene.

The resulting compound, dissolved in CH₂Cl₂, was reacted with propionic anhydride to give N⁸-propionyl-N³-(2-benzofuranyl)methyl-3,8-diazabicyclo[3.2.1]octane; m.p. 88°–90° C.

Analogously was prepared:

N⁸-propionyl-N3-(2-indolyl)methyl-3,8-diazabicyclo[3.2.1] octane; m.p. 63° C.

EXAMPLE 4

N³-benzyl-3,8-diazabicyclo[3.2.1.]octane was treated with equimolar amounts of indolyl-2-carboxylic acid chloride, as described in example 3. The resulting N⁸-(2-indolyl)carbonyl-derivative was subjected, after recovery, to hydrogenation on 10% Pd/c in ethanol in the presence of acids traces, to debenzylate the nitrogen at the 3-position. The debenzylated product was treated with SMEAH in toluene and, after recovering N⁸-(2-indolyl)methyl-3,8-diazabicyclo[3.2.1]octane, this was reacted with propionic anhydride in methylene chloride, to give the final product N⁸-(2-indolyl)methyl-N³-propionyl-3,8-diazabicyclo[3.2.1] octane.

EXAMPLE 5

Analogously to example 1, starting from N⁸-propionyl-3,8-diazabicyclo[3.2.1]octane, but using (p-cyano)cinnamyl chloride, N⁸-propionyl-N³-(p-cyano)-cinnamyl-3,8-diazabicyclo[3.2.1]octane was obtained, m.p. 87°–89° C.

The latter was subsequently subjected to acidic hydrolysis, to give the corresponding N⁸-propionyl-N³-(p-carboxy)cinnamyl-3,8-diazabicyclo[3.2.1]octane, m.p. 180°–200° C.

I claim:
1. A compounds of the formula (I)

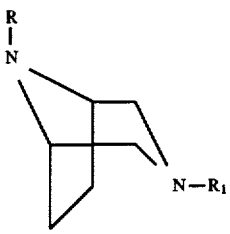

wherein

R and R₁, different from each other, are a straight or branched C₂–C₈ alkyl-carbonyl group;

a group of formula

—CH₂—(A)—B wherein:

A is a —CH=CH— group and B is a phenyl or naphthyl group optionally substituted, at the ortho-, meta- and para-positions, with one or more substituents, which are the same or different, selected from the group consisting of CONHR, carboxyl, cyano, nitro, NHCOR; or a non-benzo condensed 5 or 6- membered heterocyclic residue having at least one heteroatom selected from nitrogen, oxygen, sulfur; said heterocyclic group optionally having one or more substituents as described above for the phenyl group; or A is a single carbon-carbon bond and B is an indenyl group or a benzocondensed heterocyclic group, the heterocyclic residue being as defined above; with the proviso that when one of R or R₁ is the propionyl group, the other cannot be the cinnamyl group or the p-nitrocinnamyl group, and when R is the propionyl group, R₁ cannot be o-, or m-nitrocinnamyl or 1-naphthyl; and the pharmaceutically acceptable salts thereof.

2. A compound according to claim 1, selected from the group consisting of:

N⁸-pivaloyl-N³-(p-nitro)cinnamyl-3,8-diazabicyclo[3.2.1] octane;

N⁸-propionyl-N³-3-(2-thienyl)allyl-3,8-diazabicyclo[3.2.1] octane;

N⁸-propionyl-N³-3-[(5-nitro)-2-thienyl]allyl-3,8-diazabicyclo[3.2.1]octane;

N⁸-3-[(5-nitro)-2-thienyl]allyl-N³-propionyl-3,8-diazabicyclo[3.2.1]octane;

N⁸-propionyl-N³-(2-indolyl)methyl-3,8-diazabicyclo[3.2.1] octane;

N⁸-(2-indolyl)methyl-N³-propionyl-3,8-diazabicyclo[3.2.1] octane;

N⁸-propionyl-N³-(2-benzofuranyl)methyl-3,8-diazabicyclo [3.2.1]octane;

N⁸-(2-benzofuranyl)methyl-N³-propionyl-3,8-diazabicyclo [3.2.1]octane;

N⁸-acetyl-N³-cinnamyl-3,8-diazabicyclo[3.2.1]octane;

N⁸-valeryl-N³-cinnamyl-3,8-diazabicyclo[3.2.1]octane;

N⁸-butyryl-N³-cinnamyl-3,8-diazabicyclo[3.2.1]octane;

N⁸-butyryl-N³-(p-nitro)cinnamyl-3,8-diazabicyclo[3.2.1] octane;

N⁸-(m-nitro)cinnamyl-N³-propionyl-3,8-diazabicyclo [3.2.1]octane;

N⁸-(o-nitro)cinnamyl-N³-propionyl-3,8-diazabicyclo[3.2.1] octane;

N⁸-(p-nitro)cinnamyl-N³-butyryl-3,8-diazabicyclo[3.2.1] octane; and $N^8$-valeryl-$N^3$-(p-nitro)cinnamyl-3,8-diazabicyclo[3.2.1]octane;

$N^8$-propionyl-$N^3$-(p-carboxy)cinnamyl-3,8-diazabicyclo[3.2.1]octane;

$N^8$-propionyl-$N^3$-(p-cyano)cinnamyl-3,8-diazabicyclo[3.2.1]octane.

3. A process for the preparation of the compounds of claim 1, which comprises the steps of:

a) reacting 3,8-diazabicyclo[3.2.1]octane, suitably acylated with a straight or branched $C_2$-$C_8$ alkylcarbonyl residue at one of the two nitrogen atoms at the 3- or 8-position, with a compound of formula (II)

$$X-CH_2-(A)-B \qquad (II)$$

wherein A and B are as defined above and X is a halogen atom, and subsequently salificating, if desired.

4. A process for the preparation of the compounds of claim 1, which comprises the steps of:

a) reacting 3,8-diazabicyclo[3.2.1]octane, suitably substituted at one of the two nitrogen atoms at the 3- or 8-position, with a group of formula —$CH_2$—(A)—B wherein A and B are as defined above, with a straight or branched $C_2$-$C_8$ alkylcarbonyl chloride, and subsequently salificating, if desired.

5. A process for the preparation of compounds of claim 1, wherein $R_1$ is a —$CH_2$—(A)—B group, wherein A is a carbon-carbon bond, B is a benzocondensed heterocyclic group, optionally substituted, which process comprises the steps of:

a) reacting 3,8-diazabicyclo[3.2.1]octane, having the $N^8$ nitrogen atom protected with a suitable protecting group, with a compound of formula (III)

$$X-CO-(A)-B \qquad (III)$$

wherein A and B are as defined above and X is a halogen atom;

b) deprotecting the $N^8$ nitrogen atom;

c) reducing the $N^3$ amido group to amine;

d) acylating the $N^8$ nitrogen; and e) optionally salificating.

6. A process for the preparation of compounds of claim 1, wherein R is a —$CH_2$—(A)—B group, wherein A is a carbon-carbon bond, B is a benzocondensed heterocyclic group, optionally substituted, which process comprises the steps of:

a) reacting 3,8-diazabicyclo octane having the $N^3$ nitrogen atom protected by a protective group, with a compound of formula (III)

$$X-CO-(A)-B \qquad (III)$$

wherein A and B are as defined above and X is a halogen atom;

b) debenzylating the $N^3$ nitrogen atom;

c) reducing the $N^8$ amide group to amino group;

d) acylating the $N^3$ nitrogen atom;

e) optionally salificating.

7. Pharmaceutical compositions containing a therapeutically effective amount of one compound of claim 1 in admixture with a pharmaceutically acceptable excipient.

8. A process for the preparation of the compounds of claim 2, which comprises the steps of:

a) reacting 3,8-diazabicyclo[3.2.1]octane, suitably acylated with a straight or branched $C_2$-$C_8$ alkylcarboxyl residue at one of the two nitrogen atoms at the 3- or 8-position, with a compound of formula (II)

$$X-CH_2-(A)-B \qquad (II)$$

wherein A and B are as defined above and X is a halogen atom, and subsequently salificating, if desired.

9. A process for the preparation of the compounds of claim 2, which comprises the steps of:

a) reacting 3,8-diazabicyclo[3.2.1]octane, suitably substituted at one of the two nitrogen atoms at the 3- or 8-position, with a group of formula —$CH_2$—(A)—B wherein A and B are as defined above, with a straight or branched $C_2$-$C_8$ alkylcarboxyl chloride, and subsequently salificating, if desired.

10. A process for the preparation of compounds of claim 2, wherein $R_1$ is a —$CH_2$—(A)—B group, wherein A is a carbon-carbon bond, B is a benzocondensed heterocyclic group, optionally substituted, which process comprises the steps of:

a) reacting 3,8-diazabicyclo[3.2.1]octane, having the $N^8$ nitrogen atom protected with a suitable protecting group, with a compound of formula (III)

$$X-CO-(A)-B \qquad (III)$$

wherein A and B are as defined above and X is a halogen atom;

b) deprotecting the $N^8$ nitrogen atom;

c) reducing the $N^3$ amido group to amine;

d) acylating the $N^8$ nitrogen; and e) optionally salificating.

11. A process for the preparation of compounds of claim 2, wherein R is a —$CH_2$—(A)—B group, wherein A is a carbon-carbon bond, B is a benzocondensed heterocyclic group, optionally substituted, which process comprises the steps of:

a) reacting 3,8-diazabicyclo[3.2.1]octane having the $N^3$ nitrogen atom protected by a protective group, with a compound of formula (III)

$$X-CO-(A)-B \qquad (III)$$

wherein A and B are as defined above and X is a halogen atom;

b) debenzylating the $N^3$ nitrogen atom;

c) reducing the $N^8$ amide group to amino group;

d) acylating the $N^3$ nitrogen atom;

e) optionally salificating.

12. Pharmaceutical compositions containing a therapeutically effective amount of one compound of claim 2 in admixture with conventional carriers and excipients.

* * * * *